US006458926B1

(12) United States Patent
Evans et al.

(10) Patent No.: US 6,458,926 B1
(45) Date of Patent: *Oct. 1, 2002

(54) HETERODIMER COMPLEX OF RXR AND NURR1 OR NGFI-B

(75) Inventors: Ronald M. Evans, La Jolla, CA (US); Barry M. Forman, La Jolla, CA (US); Kazuhiko Umesono, Nara (JP)

(73) Assignee: The Salk Institute for Biological Studies, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,966

(22) Filed: Jun. 18, 1997

Related U.S. Application Data

(63) Continuation of application No. 08/372,217, filed on Jan. 13, 1995, now abandoned.

(51) Int. Cl.[7] ..................... C07K 14/435; C07K 14/705
(52) U.S. Cl. ....................................... 530/350
(58) Field of Search ................. 530/402, 350

(56) References Cited

U.S. PATENT DOCUMENTS 5,571,696 A * 11/1996 Evans et al. ............. 435/69.1
5,696,233 A * 12/1997 Evans et al. ............. 530/350
5,710,004 A * 1/1998 Evans et al. ............. 435/6

OTHER PUBLICATIONS

Schrader et al. (1994) J.B.C. 269: 6444–6449, Mar. 4, 1994.*
Perlmann et al. (1995) Genes & Development, Mar. 15, 1995.*
Ngo et al. 1994 In: The Protein Folding Problem and Tertiary Structure Prediction Merz et al. (eds.) Birkhauser Boston pp. 433, 492–495.*
Mages, et al. 1994 Molec. Endocrin. 8: 1583–1591.*
Scearce et. al. JBC (1993) 268: 8855–8861.*
Amati and Land, "Myc–Max–Mad: a transcription factor network controlling cell cycle progression, differentiation and death" *Curr. Opin. Genet. Dev.*, 4:102–108 (1994).
Andersson et al., "Thyroid hormone alters the DNA binding properties of chicken thyroid hormone receptors α and β" *Nucleic Acids Res.*, 20(18):4803–4810 (1992).
Baniahmad et al., "Modular Structure of a Chicken Lysozyme Silencer: Involvement of an Unusual Thyroid Hormone Receptor Binding Site" *Cell*, 61:505:514 (1990).

(List continued on next page.)

*Primary Examiner*—Yvonne Eyler
(74) *Attorney, Agent, or Firm*—Stephen E. Reiter; Foley & Lardner

(57) ABSTRACT

Heterodimerization is a common paradigm among eucaryotic transcription factors, though it remains unclear how individual monomers contribute to the overall transcriptional activities of the complex. The 9-cis retinoic acid receptor (RXR) serves as a common heterodimerization partner for several nuclear receptors including the thyroid hormone ($T_3R$), retinoic acid (RAR) and vitamin D receptors. A strategy has been devised to examine the transcriptional properties of each receptor individually or when tethered to a heterodimeric partner. It has been found that the intrinsic activity of RXR is masked in RXR-$T_3R$ and RXR-RAR heterodimers. In contrast, a novel RXR-Nurr1 heterodimer described herein is highly responsive to RXR ligands, suggesting that different partners exert unique allosteric control over the RXR response. These findings establish a novel 9-cis retinoic acid response pathway and resolve the paradox as to how $T_3R$, RAR and VDR contribute to distinct physiologic pathways while sharing a common RXR subunit.

10 Claims, 9 Drawing Sheets

OTHER PUBLICATIONS

Blank et al., "NF–xB and related proteins: Rel/dorsal homologies meet ankyrin–like repeats" *Trends Biochem. Sci.*, 17:135–140 (1992).

Boehm et al., "Synthesis and Structure–Activity Relationships of Novel Retinoid X Receptor–Selective Retinoids" *J. Med. Chem.*, 37:408–414 (1994).

Brown and McKnight, "Specificities of protein–protein and protein–DNA interaction of GABPα and two newly defined ets–related proteins" *Genes Dev.*, 6:2502–2512 (1992).

Bugge et al., "RXRα, a promiscuous partner of retinoic acid and thyroid hormone receptors" *Embo J.*, 11(4):1409–18 (1992).

Cheskis and Freedman, "Ligand Modulates the Conversion of DNA–Bound Vitamin $D_3$ Receptor (VDR) Homodimers into VDR–Retinoid X Receptor Heterodimers" *Mol. Cell Biol.*, 14(5):3329–3338 (1994).

Danielian et al., "Identification of a conserved region required for hormone dependent transcriptional activation by steriod hormone receptors" *Embo J.*, 11(3): 1025–1033 (1992).

Davis and Lau, "Endocrine and Neurogenic Regulation of the Orphan Nuclear Receptors Nur77 and Nur–1 in the Adrenal Glands" *Mol. Cell Biol.*, 14(5):3469–3483 (1994).

Durand et al., "Activation function 2 (AF–2) of retinoic acid receptor and 9–cis retinoic acid receptor: presence of a conserved autonomous constitutive activating domain and influence of the nature of the response element on AF–2 activity" *Embo J.* 13(22):5370–5382 (1994).

Evans, "The Steroid and Thyroid Hormone Receptor Superfamily" *Science*, 240:889–895 (1988).

Farsetti et al., "Characterization of Myelin Basic Protein Thyroid Hormone Response Element and Its Function in the Context of Native and Heterologous Promoter" *J. Biol. Chem.*, 267(22):15784–15788 (1992).

Forman et al., "Half–Site Spacing and Orientation Determines Whether Thyroid Hormone and Retinoic Acid Receptors and Related Factors Bind to DNA Response Elements as Monomers, Homodimers, or Heterodimers" *Mol. Endocrinol.*, 6(3):429–442 (1992).

Forman and Samuels, "Interactions Among a Subfamily of Nuclear Hormone Receptors: The Regulatory Zipper Model" *Mol. Endocrinol.*, 4:1293–1301 (1990).

Glass, C. K., "Differential Recognition of Target Genes by Nuclear Receptor Monomers, Dimers, and Heterodimers★" *Endocr. Rev.*, 15:391–407 (1994).

Issemann et al., "The retinoid X receptor enhances the function of the peroxisome proliferator activated receptor" *Biochimie.*, 75:251–256 (1993).

Kliewer et al., "Retinoid X receptor interacts with nuclear recetors in retinoic acid, thyroid hormone and vitamin $D_3$ signalling" *Nature*, 355:446–449 (1992).

Kliewer et al., "Convergence of 9–cis retinoic acid and peroxisome proliferator signalling pathways through heterodimer formation of their receptors" *Nature*, 358:771–774 (1992).

Kurokawa et al., "Differential orientations of the DNA–binding domain and carboxyterminal dimerization interface regulate binding site selection by nuclear receptor heretordimes" *Genes Dev,*, 7:1423–1435 (1993).

Ladias et al., "Regulation of the Apolipoprotein AI Gene by ARP–1, a Novel Member of the Steroid Receptor Superfamily" *Science*, 251:561–565 (1991).

Lamb and McKnight, "Diversity and specificity in transcriptional regulation: the benefits of heterotypic dimerization-"*Trends Biochem. Sci.*, 16:417–422 (1991).

Law et al., "Identification of a New Brain–Specific Transcription Factor, NURRI" *Mol. Endocrinol.*, 6:2129–2135 (1992).

Lee et al., "Structure of the Retinoid X Receptor α, DNA Binding Domain: A Helix Required for Homodimeric DNA Binding" *Science*, 260:1117–1121 (1993).

Leid et al, "Purification, Cloning, and RXR Identity of the HeLa Cell Factor with Which RAR or TR Heterodimerizes to Bind Target Sequences Efficiently" *Cell*, 68:377–395 (1992).

Luisi et al., "Crystallographic analysis of the interaction of the glucocorticoid receptor with DNA" *Nature*, 352:497–505 (1991).

MacDonald et al, "Retinoid X Receptors Stimulate and 9–cis Retionic Acid Inhibits 1,25–Dihydroxyvitamin $D_3$–Activated Expression of the Rat Osteocalcin Gene" *Mol. Cell Biol.*, 13(9):5907–5917 (1993).

Mangelsdorf et al., "A Direct Repeat in the Cellular Retinol–Binding Protein II Gene Confers Differential Regulation by RXR and RAR" *Cell*, 66:555–561 (1991).

Marks et al., "H–2RIIBP (RXRβ) heterodimerization provides a mechanism for combinatorial diversity in the regulation of retinoic acid and thyroid hormone responsive genes" *EMBO J.* 11(4):1419–1435 (1992).

Minucci et al., "Dominant Negative Retinoid X Receptor β Inhibits Retinoic Acid–Responsive Gene Regulation in Embryonal Carcinoma Cells" *Mol. Cell Biol.* 14(1):360–372 (1994).

Miyajima et al., "Identification of two novel members of erbA superfamily by molecular cloning: the gene products of the two are highly related to each other" *Nucleic Acids Research*, 16: 11057–11074 (1988).

Mlodzik et al., "The Drosophila seven–up Gene, a Member of the Steroid Receptor Gene Superfamily, Controls Photoreceptor Cell Fates" *Cell*, 60: 211–244 (1990).

Naar et al., "The Orientation and Spacing of Core DNA–Binding Motifs Dictate Selective Transcriptional Responses to Three Nuclear Receptors" *Cell*, 65:1267–1279 (1991).

Nagpal et al., "RARs and RXRs: evidence for two autonomous transactivation functions (AF–1 and AF–2) and heterodimerization *in vivo*" *EMBO J.*, 12(6):2349–2360 (1993).

Oro et al., "Relationship between the product of the *Drosophila ultraspiracle* locus and the vertebrate retinoid X receptor" *Nature*, 347: 298–301 (1990).

Perlmann et al., "Determinants for selective RAR and TR recognition of direct HREs" *Genes Dev.*, 7:1411–1422 (1993).

Raisher et al., "Identification of a Novel Retinoid–responsive Element in the Promoter Region of the Medium Chain Acyl–Coenzyme A Dehydrogenase Gene" *J. Biol. Chem.* 267(28):20264–20269 (1992).

Ribiero et al., "Thyroid Hormone Alters in Vitro DNA Binding of Monomers and Dimers of Throiud Hormone Receptors" *Mol. Endocrinol.*, 6:1142–1152 (1992).

Sadowski and Ptashne, "A vector for expressing GAL4(1–147) fusions in mammalian cells" *Nucleic Acids Res.*, 17:7539 (1989).

Samuels et al., "Depletion of L–3,5,3'–Triiodothyronine and in L–Thyroxine in Euthyroid Calf Serum for Use in Cell Culture Studies of the Action of Thyroid Hormone★" *Endocrinology*, 105(1):80–85 (1979).

Scearce et al., "RNR–1, a Nuclear Receptor in the NGFI–B/Nur77 Family That Is Rapidly Induced in Regenerating Liver★" *J. Biol. Chem.* 268(12):8855–8861 (1993).

Schwabe et al., "The Crystal Structure of the Estrogen Receptor DNA–Binding Domain Bound to DNA: How Receptors Discriminate between Their Response Elements" *Cell*, 75:567–578 (1993).

Sladek et al., "Liver–enriched transcription factor HNF–4 is a novel member of the steroid hormone receptor family" *Genes & Development*, 4: 2353–2365 (1990).

Tini et al., "An everted repeat mediates retinoic acid induction of the γF–crystallin gene: evidence of a direct role for retinoid in lens development" *Genes Dev.*, 7:295–307 (1993).

Toney et al., "Conformational Changes in Chicken Thyroid Hormone Receptor α1 Induced by Binding to Ligand or to DNA" *Biochemistry*, 32:2–6 (1993).

Towers et al., "DNA target selectivity by the vitamin $D_3$ receptor: Mechanism of dimer binding to an asymmetric repeat element" *Proc. Natl. Acad. Sci. USA*, 90:6310–6314 (1993).

Umesono et al., "Direct Repeats as Selective Response Elements for the Thyroid Hormone, Retinoic Acid, and Vitamin $D_3$ Receptors" *Cell*, 65:1255–1266 (1991).

Umesono et al., "Retinoic acid and thyroid hormone induce gene expression through a common responsive element" *Nature*, 336:262–265 (1988).

Wang et al., "COUP transcription factor is a member of the steroid receptor superfamily" *Nature*, 340:163–166 (1989).

Williams et al., "Oligomeric Binding of T3 Receptor Is Required for Maximal Te Response★" *J. Biol. Chem.*, 266:19636–19644 (1991).

Wilson et al., "The Orphan Receptors NGFI–B and Steroidogenic Factor 1 Establish Monomer Binding as a Third Paradigm of Nuclear Receptor–DNA Interaction" *Mol. Cell Biol.*, 13(9):5794–5804 (1993).

Wilson et al., "Participation of Non–Zinc Finger Residues in DNA Binding by Two Nuclear Orphan Receptors" *Science* 256:107–110 (1992).

Yao et al., "Functional ecdysone receptor is the product of *ECR* and *Ultraspiracle genes*" *Nature*, 366:476–479 (1993).

Yen et al., "Triiodothyronine ($T_3$) Decreases Binding to DNA by $T_3$–Receptor Homodimers but Not Receptor–Auxiliary Proten Heterodimerws★" *J. Biol. Chem.*, 267(6):3565–3568 (1992).

Yu et al., "RXRβ: A Coregulator That Enhances Binding of Retinoic Acid, Thyroid Hormone, and Vitamin D Receptors to Their Cognate Response Elements" *Cell*, 67:1251–1266 (1991).

Zechel et al., "Dimerization interfaces formed between the DNA binding domains determine the cooperative binding of RXR/RAR and RXR/TR heterodimers to DR5 and DR4 elements" *EMBO J.*, 13(6):1414–1424 (1994).

Zenke et al., "V–erbA Oncogene Activation Entails the Loss of Hormone–Dependent Regulator Activity of c–erbA" *Cell*, 61:1035–1049 (1990).

Zhang et al., "Retinoid X receptor is an auxiliary protein for thyroid hormone and retinoic acid receptors" *Nature*, 355:441–446 (1992).

Amati and Land, "Myc—Max—Mad: a transcription factor network controlling cell cycle progression, differentiation and death" *Curr. Opin. Genet. Dev.* 4:102–108 (1994).

Andersson, et al., "Thyroid hormone alters the DNA binding properties of chicken thyroid hormone receptors α and β" *Nucleic Acids Res.* 20:4803–4810 (1992).

Baniahmad et al., "Modular Structure of a Chicken Lysozyme Silencer: Involvement of an Unusual Thyroid Hormone Receptor Binding Site" *Cell* 61:505–514 (1990).

Blank et al., "$NF_{-K}B$ and related proteins: Rel/dorsal homologies meet ankyrin–like repeats" *Trends Biochem. Sci.* 17:135–140 (1992).

Boehm, et al., "Synthesis and Structure—Activity Relationships of Novel Retinoid X Receptor–Selective Retinoids" *J. Med. Chem.* 37:408–414 (1994).

Brown and McKnight, "Specificities of protein—protein and protein—DNA interaction of GABPα and two newly defined ets–related proteins" *Genes & Dev.* 6:2502–2512 (1992).

Bugge, et al., "RXRα, a promiscuous partner of retinoic acid and thyroid hormone receptors" *EMBO J.* 11:1409–1418 (1992).

Cheskis and Freedman, "Ligand Modulates the Conversion of DNA–Bound Vitamin $D_3$ Receptor (VDR) Homodimers into VDR–Retinoid X Receptor Heterodimers" *Mol. Cell Biol.* 14:3329–3338 (1994).

Danielian, et al., "Identification of a conserved region required for hormone dependent transcriptional activation by steroid hormone receptors" *EMBO J.* 11:1025–1033 (1992).

Davis and Lau, "Endocrine and Neurogenic Regulation of the Orphan Nuclear Receptors Nur77 and Nurr–1 in the Adrenal Glands" *Mol. Cell Biol.* 14:3469–3483 (1994).

Durand, et al., "Activation function 2 (AF–2) of retinoic acid receptor and 9–cis retinoic acid receptor: prescence of a conserved autonomous constitutive activating domain and influence of the nature of the response element on AF–2 activity" *EMBO J.* 13:5370–5382 (1994).

Evans, "The Steroid and Thyroid Hormone Receptor Superfamily" *Science* 240:889–895 (1988).

Farsetti, et al., "Characterization of Myelin Basic Protein Thyroid Hormone Response Element and Its Function in the Context of Native and Heterologous Promoter" *J. Biol. Chem.* 267:15784–15788 (1992).

Forman and Samuels, "Interactions Among a Subfamily of Nuclear Hormone Receptors: The Regulatory Zipper Model" *Mol. Endocrinol.* 4:1293–1301 (1990).

Forman, et al., "Half–Site Spacing and Orientation Determines Whether Thyroid Hormone and Retinoic Acid Receptors and Related Factors Bind to DNA Response Elements as Monomers, Homodimers, or Heterodimers" *Mol. Endocrinol.* 6:429–442 (1992).

Glass, "Differential Recognition of Target Genes by Nuclear Receptor Monomers, Dimers, and Heterodimers" *Endocr. Rev.* 15:391–407 (1994).

Issemann, et al., "The retinoid X receptor enhances the function of the peroxisome proliferator activated receptor" *Biochimie* 75:251–256 (1993).

Kliewer, et al., "Convergence of 9–cis retinoic acid and peroxisome proliferator signalling pathways through heterodimer formation of their receptors" *Nature* 358:771–774 (1992).

Kliewer, et al., "Retinoid X receptor interacts with nuclear receptors in retinoic acid, thyroid hormone and vitamin $D_3$ signalling" *Nature* 355:446–449 (1992).

Kurokawa, et al., "Differential orientations of the DNA—binding domain and carboxy–terminal dimerization interface regulate binding site selection by nuclear receptor heterodimers" *Genes Dev.* 7:1423–1435 (1993).

Ladias and Karathanasis, "Regulation of the Apolipoprotein AI Gene by ARP–1, a Novel Member of the Steroid Receptor Superfamily" *Science* 251:561–565 (1991).

Lamb and McKnight, "Diversity and specificity in transcriptional regulation: the benefits of heterotypic dimerization" *Trends Biochem. Sci.* 16:417–422 (1991).

Law, et al., "Identification of a New Brain–Specific Transcription Factor, NURR1" *Mol. Endocrinol.* 6:2129–2135 (1992).

Lee, et al., "Structure of the Retinoid X Receptor α DNA Binding Domain: A Helix Required for Homodimeric DNA Binding" *Science* 260:1117–1121 (1993).

Leid, et al., "Purification, Cloning, and RXR Identity of the HeLa Cell Factor with Which RAR or TR Heterodimerizes to Bind Target Sequences Efficiently" *Cell* 68:377–395 (1992).

Luisi, et al., "Crystallographic analysis of the interaction of the glucocorticoid receptor with DNA" *Nature* 352:497–505 (1991).

MacDonald, et al., "Retinoid X Receptors Stimulate and 9–cis Retinoic Acid Inhibits 1,25–Dihydroxyvitamin $D_3$–Activated Expression of the Rat Osteocalcin Gene" 13:5907–5917 (1993).

Mangelsdorf, et al., "A Direct Repeat in the Cellular Retinol–Binding Protein Type II Gene Confers Differential Regulation by RXR and RAR" *Cell* 66:555–561 (1991).

Marks, et al., "H–2RIIBP (RXRβ) heterodimerization provides a mechanism for combinatorial diversity in the regulation of retinoic acid and thyroid hormone responsive genes" *EMBO J.* 11:1419–1435 (1992).

Minucci, et al., "Dominant Negative Retinoid X Receptor β Inhibits Retinoic Acid–Responsive Gene Regulation in Embryonal Carcinoma Cells" *Mol. Cell Biol.* 14:360–372 (1994).

Miyajima, et al., "Identification of two novel members of erbA superfamily by molecular cloning: the gene products of the two are highly related to each other" *Nucleic Acids Research* 16:11057–11074 (1988).

Mlodzik, et al., "The Drosophila seven–up Gene, a Member of the Steroid Receptor Gene Superfamily, Controls Photoreceptor Cell Fates" *Cell* 60:211–224 (1990).

Näär, et al., "The Orientation and Spacing of Core DNA–Binding Motifs Dictate Selective Transcriptional Responses to Three Nuclear Receptors" *Cell* 65:1267–1279 (1991).

Nagpal, et al., "RARs and RXRs: evidence for two autonomous transactivation functions (AF–1 and AF–2) and heterodimerization in vivo" *EMBO J.* 12:2349–2360 (1993).

Oro, et al., "Relationship between the product of the *Drosophila ultraspiracle* locus and the vertebrate retinoid X receptor" *Nature* 347:298–301 (1990).

Perlmann, et al., "Determinants for selective RAR and TR recognition of direct repeat HREs" *Genes & Dev.* 7:1411–1422 (1993).

Raisher, et al., "Identification of a Novel Retinoid–responsive Element in the Promoter Region of the Medium Chain Acyl–Coenzyme A Dehydrogenase Gene" *J. Biol. Chem.* 267:20264–20269 (1992).

Ribeiro, et al., "Thyroid Hormone Alters in Vitro DNA Binding of Monomers and Dimers of Thyroid Hormone Receptors" *Mol. Endocrinol.* 6:1142–1152 (1992).

Sadowski and Ptashne, "A vector for expressing GAL4(1–147) fusions in mammalian cells" *Nucleic Acids Research* 17:7539 (1989).

Samuels, et al., "Depletion of $_L$–3,5,3'–Triiodothyronine and $_L$–Thyroxine in Euthyroid Calf Serum for Use in Cell Culture Studies of the Action of Thyroid Hormone" *Endocrinol.* 105:80–85 (1979).

Scearce, et al., "RNR–1, a Nuclear Receptor in the NGFI–B/Nurr77 Family That Is Rapidly Induced in Regenerating Liver" *J. Biol. Chem.* 268:8855–8861 (1993).

Schwabe, et al., "The Crystal Structure of the Estrogen Receptor DNA–Binding Domain Bound to DNA: How Receptors Discriminate between Their Response Elements" *Cell* 75:567–578 (1993).

Sladek, et al., "Liver–enriched transcription factor HNF–4 is a novel member of the steroid hormone receptor superfamily" *Genes & Dev.* 4:2353–2365 (1990).

Tini, et al., "An everted repeat mediates retinoic acid induction of the γF–crystallin gene: evidence of a direct role for retinoids in lens development" *Genes & Dev.* 7:295–307 (1993).

Toney, et al., "conformational Changes in chicken Thyroid Hormone Receptor α1 Induced by Binding to Ligand or to DNA" *Biochem.* 32:2–6 (1993).

Towers, et al.. "DNA target selectivity by the vitamin $D_3$ receptor: Mechanism of dimer binding to an asymmetric repeat element" 90:6310–6314 (1993).

Umesono, et al., "Retinoic acid and thyroid hormone induce gene expression through a common responsive element" *Nature* 336:262–265 (1988).

Wang, et al., "COUP transcription factor is a member of the steroid receptor superfamily" *Nature* 340:163–166 (1989).

Williams, et al., "Oligomeric Binding of T3 Receptor Is Required for Maximal T3 Response" *J. Biol. Chem.* 266:19636–19644 (1991).

Wilson, et al., "The Orphan Receptors NGFI–B and Steroidogenic Factor 1 Establish Monomer Binding as a Third Paradigm of Nuclear Receptor–DNA Interaction" *Mol. Cell Biol.* 13:5794–5804 (1993).

Wilson, et al., "Participation of Non–Zinc Finger Residues in DNA Binding by Two Nuclear Orphan Receptors" *Science* 256:107–110 (1992).

Yao, et al., "Functional ecdysone receptor is the product of EcR and Ultraspiracle genes" *Nature* 366:476–479 (1993).

Yen, et al., "Triiodothyronine ($T_3$) Decreases Binding to DNA by $T_3$–Receptor Homodimers but Not Receptor–Auxiliary Protein Heterodimers" *J. Biol. Chem.* 267:3563–3568 (1992).

Yu, et al., "RXRβ: A Coregulator That Enhances Binding of Retinoic Acid, Thyroid Hormone, and Vitamin D Receptors to Their Cognate Response Elements" *Cell* 67:1251–1266 (1991).

Zechel, et al., "Dimerization interfaces formed between the DNA binding domains determine the cooperative binding of RXR/RAR and RXR/TR heterodimers to DR5 and DR4 elements" *EMBO J.* 13:1414–1424 (1994).

Zenke, et al., "V–erbA Oncogene Activation Entails the Loss of Hormone–Dependent Regulator Activity of c–erbA" *Cell* 61:1035–1049 (1990).

Zhang, et al., "Retinoid X receptor is an auxiliary protein for thyroid hormone and retinoic acid receptors" *Nature* 355:441–446 (1992).

\* cited by examiner

HETERODIMER COMPLEX OF RXR AND NURR1 OR NGFI-B

This application is a continuation of application Ser. No. 08/372,217, filed Jan. 13, 1995 now abandoned.

FIELD OF THE INVENTION

The present invention relates to intracellular receptors, and method for the modulation thereof. In a particular aspect, th present invention relates to novel heterodimeric complexes. In another aspect, the present invention relates to methods for modulating processes mediated by retinoid X receptor and/or orphan receptor Nurr1.

BACKGROUND OF THE INVENTION

Heterodimerization is a common theme in eucaryotic regulatory biology. Indeed, a number of transcription factor families have been defined by their characteristic dimerization interface. These include the leucine zipper (e.g. fos, jun, CREB, C/EBP; see, for example, Lamb and McKnight, in *Trends Biochem. Sci.* 16:417–422 (1991)), helix-loop-helix (e.g. myc, max, MyoD, E12, E47; see, for example, Amati and Land, in *Curr. Opin. Genet. Dev.* 4:102–108 (1994)), rel (NFkB, dorsal; see, for example, Blank et al., in *Trends Biochem. Sci.* 17:135–140 (1992)), ankyrin (GABP; see, for example, Brown and McKnight, in *Genes Dev.* 6:2502–2512 (1992)), and the nuclear receptor superfamilies (see, for example, Evans, in *Science* 240:889–895 (1988), and Forman and Samuels, *Mol. Endocrinol.* 4:1293–1301 (1990)). Detailed analyses of these proteins have shown that heterodimerization produces novel complexes that bind DNA with higher affinity or altered specificity relative to the individual members of the heterodimer (see, for example, Glass, in *Endocr. Rev.* 15:391–407 (1994)). Indeed, little is known about the contributions of each monomer toward the transcriptional properties of the complex.

Nuclear hormone receptors are characterized by a central DNA binding domain (DBD, see FIG. 1), which targets the receptor to specific DNA sequences, known as hormone response elements (HREs). The retinoic acid receptor (RAR), the thyroid hormone receptor ($T_3R$), the vitamin $D_3$ receptor (VDR) and the fatty acid/peroxisome proliferator activate receptor (PPAR) preferentially bind to DNA as heterodimers with a common partner, the retinoid X (or 9-cis retinoic acid) receptor (RXR; see, for example, Yu et al., in *Cell* 67:1251–1266 (1991); Bugge et al., in *EMBO J.* 11:1409–18(1992); Kliewer et al., in *Nature* 355:446–449 (1992); Leid et al, in *Cell* 68:377–395 (1992); Marks et al., in *EMBO J.* 11:1419–1435 (1992); Zhang et al., in *Nature* 355:441–446( (1992); and Issemann et al., in *Biochimie.* 75:251–256 (1993).

Naturally occurring HREs are composed of direct repeats (i.e., DRs; see Umesono et al., in *Cell* 65:1255–1266 (1991), inverted repeats (i.e., IRs; see Umesono et al., in *Nature* 336:262–265 (1988), and Williams et al. in *J. Biol. Chem.* 266:19636–19644 (1991)), and/or everted repeats (ERs; see Baniahmad et al., in *Cell* 61:505–514 (1990); Farsetti et al., in *J. Biol. Chem.* 267:15784–15788 (1992); Raisher et al., in *J. Biol. Chem.* 267:20264–20269 (1992); or Tini et al., in *Genes Dev.* 7:295–307 (1993)) of a degenerate $X_n$-AGGTCA core-site.

The DNA binding domain (DBD) contains two helical regions, one of which serves as a recognition helix that makes base-specific contacts within the major groove of the core-site (see, for example, Luisi et al., in *Nature* 352:497–505 (1991) an Schwabe et al., in *Cell* 75:567–578 (1993)). A third helix has been identified in some receptors which makes additional minor groove contacts in the 5' portion of the core-binding site, $X_n$ (see, for example, Wilson et a ., in *Science* 256:107–110 (1992) or Lee et al., in *Science* 260:1117–1121 (1993)).

In direct repeats (DR, head-to-tail arrangement), the $X_n$ sequence also serves as a gap which separates the two core-binding sites. Spacers of 1, 3, 4 and 5 nucleotides serve as preferred response elements for heterodimers of RXR with PPAR, VDR, $T_3R$ and RAR, respectively (see, for example, Naar et al., in *Cell* 65:1267–1279 (1991); Umesono et al., 1991, supra; Kliewer et al., in *Nature* 358:771–774 (1992); and Issemann et al., supra). The optimal gap length for each heterodimer is determined by protein—protein contacts which appropriately position the DBDs of RXR and its partner (see, for example, Kurokawa et al., in *Genes Dev.* 7:1423–143 (1993); Perlmann et al., in *Genes Dev.* 7:1411–1422 (1993); Towers et al., in *Proc. Natl. Acad. Sci. USA* 90:6310–6314 (1993); and Zechel et al., in *EMBO J.* 13:1414–1424 (1994)). In contrast to this mode of DNA binding, a growing number of receptor-like proteins have been identified which bind as a monomer to a single core-site. The NGFI-b/Nurr1 orphan receptors provide well characterized example of this paradigm (Wilson et al., in *Mol. Cell Biol.* 13:5794–5804 (1993)).

Once bound to an HRE, each receptor responds to its signal through the C-terminal ligand binding domain (LBD), which binds its cognate hormone with high affinity and specificity (see, for example, Evans, 1988, supra; or Forman and Samuels, 1990, supra). The LBD is a complex entity containing several embedded subdomains. These include a C-terminal transactivation function ($\tau 2$), a series of heptad repeats which serve as a dimerization interface and a poorly-delineated transcriptional suppression domain (see FIG. 1, and Forman and Samuels, 1990, supra).

The transactivation domain, $\tau 2$, consists of approximately 20 amino acids with the potential to form an amphipathic $\alpha$-helix (see Zenke et al., in *Cell* 61:1035–1049 (1990); Danielian et al., in *EMBO J.* 11:1025–1033 (1992); Nagpal et al., in *EMBO J.* 12:2349–2360 (1993) ; and Durand et al., in *EMBO J.* 13: 5370–5382 (1994)). When linked to a heterologous DNA binding domain, the isolated T2 domain displays constitutive transcriptional activity. However, in the natural context of the LBD, transcriptional activity requires the addition of ligand.

The above-described evidence indicates that the LBD functions as a modular unit whose transcriptional activities are controlled by ligand. Accordingly, it should be possible for both members of a receptor heterodimer to be simultaneously activated by specific ligands therefor. However, in spite of this possibility, it has been discovered that the ligand-induced transcriptional activities of various receptor subtypes vary as a function of the partner with which a subtype participates in the formation of a heterodimer. For example, the ligand-induced transcriptional activities of RXR are suppressed when complexed with RAR and $T_3R$. This suppression occurs at the level of ligand binding and transcriptional activation. Furthermore, RXR responsiveness has not been observed with other partners, including VDR.

Accordingly, the identification of receptor subtypes which participate in the formation of RXR- containing heterodimers, yet retain the ability to be activated by RXR-selective ligands, would be highly desirable. The present invention identifies such receptor subtypes and provides methodology for identifying additional receptor species having such properties.

BRIEF DESCRIPTION OF THE INVENTION

In accordance with the present invention, it has been discovered that RXR can interact productively with Nurr1, a member of the nuclear receptor superfamily that (in the absence of heterodimerizing partner therefor) is capable of binding DNA as a monomer (see, for example, Law et al., in *Mol. Endocrinol.* 6:2129–2135 (1992); and Scearce et al., in *J. Biol. Chem.* 268:8855–8861 (1993)). As a result of this interaction, the constitutive activity of Nurr1 is suppressed, and the resulting complex becomes responsive to RXR-selective ligands (e.g., 9-cis retinoic acid). The unique ability of the Nurr1-RXR heterodimer complex to transduce RXR signals establishes a novel response pathway.

The result described herein suggest that heterodimer formation imparts allosteric changes upon the ligand binding domain (LBD) of nuclear receptors. These allosteric changes confer transcriptional activities onto the heterodimer that are distinct from those of the component monomers. This arrangement permits a limited number of regulatory proteins to generate a diverse set of transcriptional responses to multiple hormonal signals.

BRIEF DESCRIPTION OF THE FIGURES

FIG. 6 collectively illustrates that the ligand binding activity of RXR is altered by $T_3R$ and RAR.

FIG. 7 collectively demonstrates that a novel Nurr1-RXR complex provides a signaling pathway for 9-cis retinoic acid.

Thus.

DETAILED DESCRIPTION OF THE INVENTION

Figure 1:
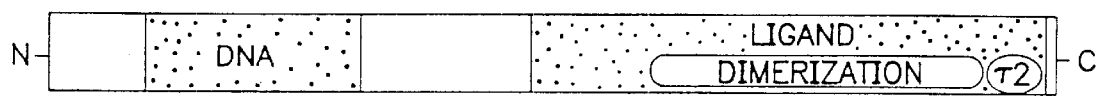
FIG. 1 schematically represents the functional domains of nuclear hormone receptors. "DNA" represents the DNA binding domain. "LIGAND" represents the large C-terminal ligand binding domain. Dimerization and transactivation (τ2) functions are embedded within this region, as illustrated

In accordance with the present invention, there is provided a heterodimer complex comprising RXR and a silent partner therefore.

As employed herein, the term "silent partner" refers to members of the steroid/thyroid superfamily of receptors which are capable of forming heterodimeric species with RXR, wherein the silent partner of the heterodimer is not capable of binding ligand (i.e., only the RXR co-partner of the heterodimer is capable of binding ligand).

As employed herein, the phrase "members of the steroid/thyroid superfamily of receptors" (also known as "nuclear receptors" or "intracellular receptors") refers to hormone binding proteins that operate as ligand-dependent transcription factors, including identified members of the steroid/thyroid superfamily of receptors for which specific ligands have not yet been identified (referred to hereinafter as "orphan receptors"). These hormone binding proteins have the intrinsic ability to bind to specific DNA sequences. Following binding, the transcriptional activity of target gene (i.e., a gene associated with the specific DNA sequence) is modulated as a function of the ligand bound to the receptor.

The DNA-binding domains of all of these nuclear receptors are related, consisting of 66–68 amino acid residues, and possessing about 20 invariant amino acid residues, including nine cysteines.

A member of the superfamily can be identified as a protein which contains the above-mentioned invariant amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids B8–153). The highly conserved amino acids of the DNA-binding domain of members of the superfamily are as follows:

Cys-X-X-Cys-X-X-Asp*-X-Ala*-X-(1Gly*-X-Tyr*-X-X-X-X-Cys-X-X-Cys-Lys*-X-Phe-Phe-X-Arg*-X-X-X-X-X-X-X-X-(X-X-) Cys-X-X-X-X-X-(X-X-X-) Cys-X-X-X-Lys-X-X-Arg-X-X-Cys-X-X-Cys-Arg*-X-X-Lys*-Cys-X-X-X-Gly*-Met (SEQ ID No 1);

wherein X designates non-conserved amino acids within the DNA-binding domain, the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Examples of silent partners contemplated for use in the practice of he present invention are various isoform(s) of Nurr1, HNF4 [see, for example, Sladek et al., in Genes & Development 4: 2353–2365 (1990)], the COUP family of receptors [see, for example, Miyajima et al., in Nucleic Acids Research 16: 11057–11074 (1988), Wang et al., in Nature 340: 163–166 (1989)], COUP-like receptors and COUP homologs, such as those described by Mlodzik et al., in Cell 60: 211–224 (990) and Ladias et al., in Science 251: 561–565 (1991), the ultraspiracle receptor [see, for example, Oro et al., in Nature 347: 298–301 (1990)], and the like.

RXR species contemplated for use in the practice of the present invention are selected from RXRα, RXRβ, RXRγ, and the like.

In accordance with another embodiment of the present invention, there is provided a method to suppress the constitutive activity of Nurr1. Such method comprises contacting Nurr1 with at least the ligand binding domain of RXR.

In accordance with yet another embodiment of the present invention, there is provided a method to render Nurr1-containing cell inducibly responsive to RXR selective ligands. Such method comprises contacting such cells with at least the ligand binding domain of RXR.

In accordance with still another embodiment of the present invention, there is provided a method to render RXR-containing cells responsive to RXR selective ligands. Such method comprises contacting said cells with a silent partner therefor.

In accordance with a further embodiment of the present invention, there is provided a method for the identification of nuclear receptor(s) which participate as silent partner(s) in the formation of a heterodimer with RXR. Such method comprises
introducing into a cell:
  at least the ligand binding domain of a putative silent partner for RXR,
  a chimeric construct containing a GAL4 DNA binding domain and at least the ligand binding domain of RXR, and
  a reporter construct, wherein said reporter construct comprises:
    (a) a promoter that is operable in said cell,
    (b) a GAL4 response element (or a response element for the putative silent partner, when substantially full length putative receptor is employed), and
    (c) DNA encoding a reporter protein,
      wherein said reporter protein-encoding DNA is operatively linked to said promoter for transcription of said DNA, and
      wherein said GAL4 response element is operatively linked to said promoter for activation thereof, and thereafter
monitoring expression of reporter upon exposure of the above-described cell to RXR selective ligand(s).

In accordance with a still further embodiment of the present invention, there is provided a method for identifying ligands selective for heterodimers comprising RXR and a silent partner therefor. Such method comprises
  comparing the level of expression of reporter when cells containing a reporter construct, RXR and silent partner therefor are exposed to test compound, relative to the level of expression of reporter when cells containing a reporter construct, RXR and a member of the steroid/thyroid superfamily which is not a silent partner therefor are exposed to test compound, and
  selecting those compounds which activate only the combination of RXR and silent partner therefor.

The LBD of nuclear hormone receptors is a complex multifunctional unit containing subdomains for dimerization, transcriptional suppression and hormone-induced transactivation (Forman and Samuels, 1990, supra). The dimerization domain includes a series of heptad repeats flanked by sequences required for ligand binding. Thus, the dimerization domain is embedded within the larger LBD. This structural arrangement raises the possibility that dimerization may serve as an allosteric modulator of ligand binding and transactivation. This possibility has been investigated with the following observations.

First, dimerization within the LBD is utilized to confer transcriptional suppression upon certain heterodimeric complexes. This is exemplified by unliganded $T_3R$ and RAR, which confer transcriptional suppression upon RXR. Similarly, in accordance with the present invention, it is demonstrated that RXR can suppress constitutive activation by Nurr1.

Second, the intrinsic ligand binding capacity of the LBD can be modulated by dimerization. This is illustrated by the ability of unliganded RAR to abrogate the ligand binding activity of RXR. It has also been found that $T_3R$ induces a similar suppression, but the presence of ligand therefor, i.e., $T_3$, is required for the complete effect. Thus, RXR is seen to serve as a silent partner when participating in the $T_3R$ and RAR pathways.

However, not all heterodimeric interactions restrict ligand-responsiveness. Indeed, in accordance with the present invention, it is demonstrated that RXR actively confers ligand-responsiveness upon the Nurr1-RXR heterodimer complex. Similarly, it has previously been shown that the Drosophila ecdysone receptor (EcR) acquires ligand binding activity after heterodimerization with USP (Drosophila homolog of RXR; see Yao et al., in Nature 366:476–479 (1993)). Thus, differential interactions among receptor LBDs can either restrict, redirect or lead to an acquisition of new ligand binding phenotypes.

Figure 8:
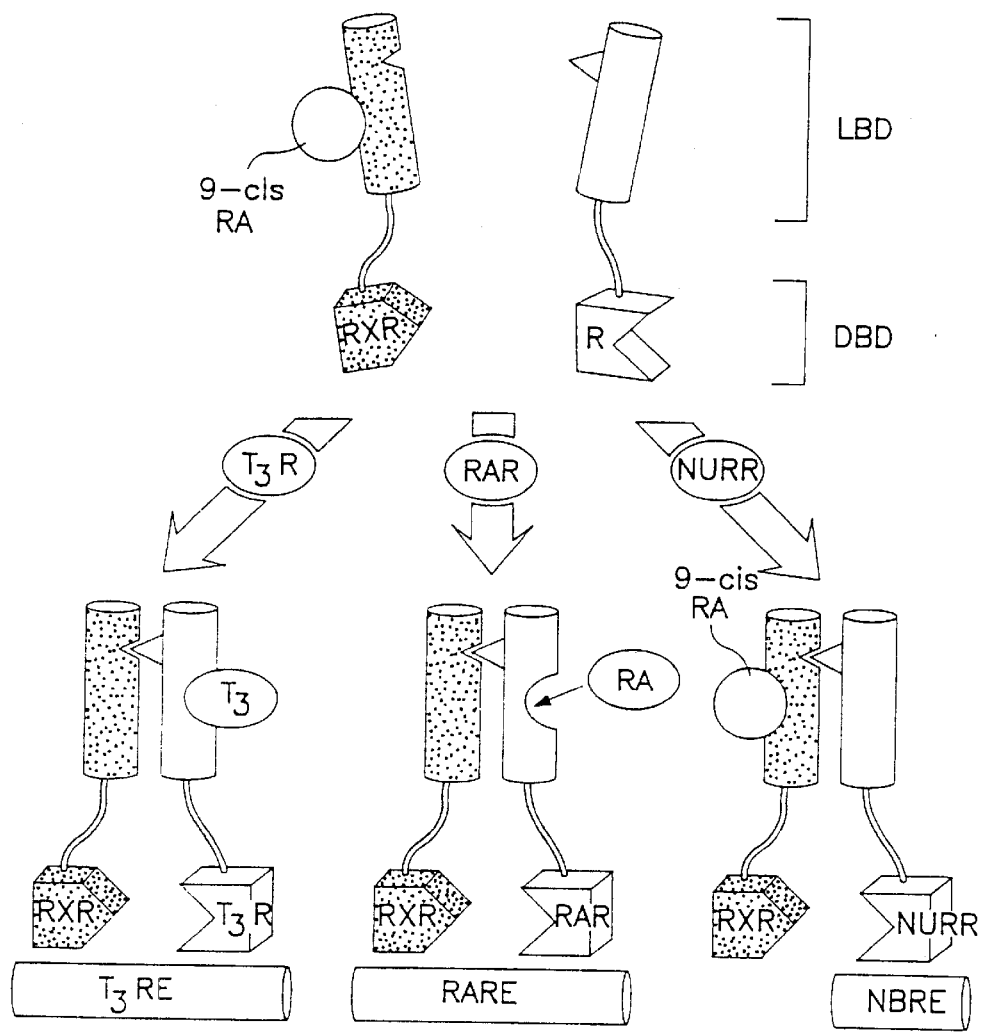
FIG. 8 presents an allosteric control model of ligand responsiveness.

In accordance with the results described herein, a structural model is proposed (see FIG. 8) to account for the observations. In FIG. 8, RXR (dark shading) and its partner receptor (e.g., $T_3R$, RAR or Nurr1 (designated "R" in the figure, shown in light shading) initially exist as monomers in solution. RXR in monomeric form is capable of binding ligand. RXR-receptor heterodimers then form, driven by the dimerization interface that is embedded within the ligand binding domain (LBD). Subsequent to dimerization, binding of ligand (e.g., 9-cis RA) to RXR is modestly reduced by $T_3R$ and dramatically reduced by RAR. Addition of ligand for $T_3R$ (e.g., $T_3$) results in a further reduction in 9-cis RA binding, while certain retinoids (shown as "RA" in the figure) such as Am580 (an RAR specific ligand) may restore 9-cis RA binding to RXR—RAR. It is of particular note that the Nurr1-RXR heterodimer maintains the ability to bind 9-cis RA.

The above-described structural model relies on the observation that a major dimerization interface is embedded within the larger LBD. It is proposed that upon dimerization, the structure of the RXR ligand binding/dimerization domain is altered. Each RXR partner gives rise to unique conformational changes that either maintain or abrogate RXR ligand binding activity. Binding of ligand by the partner receptor induces a conformational change that can be propagated through the dimerization interface onto the LBD of RXR. This model allows one to explain how the dimerization partner and its specific ligand exert allosteric control over the RXR ligand response.

In the above-described model, the RXR monomer (or homodimer) is capable of binding ligand with high affinity. When RXR interacts with one of its non-permissive partners (i.e., T$_3$R or RAR), its ability to bind ligand is diminished. On the other hand, dimerization of USP/RXR with EcR promotes high affinity binding of ecdysone to EcR. It is believed that these effects are a direct consequence of the localization of a major dimerization interface within the LBD (see FIGS. 1 and 8). The above-described model predicts that this structural arrangement serves to functionally link dimerization and ligand binding activities. This would then provide a mechanism by which dimerization could exert allosteric control over the ligand response.

In addition to dimerization, ligand binding by one receptor may also result in allosteric modification of its partner. Specifically, binding of ligand to the RXR partner can either restore (as in the case of RAR) or further decrease (as in the case of T$_3$R) the ligand binding potential of RXR (see FIG. 6). It is already known that upon ligand binding the cognate receptor undergoes a conformation change (see, for example, Toney et al., in *Biochemistry* 32:2–6 ( 993)). The results provided herein support the suggestion that ligand-induced conformation changes in the LBD of one heterodimer partner will be propagated through the dimerization interface onto the LBD of the partner. Thus, the model presented above can explain how a dimerization partner and its specific ligand can exert allosteric control over the RXR ligand response. Similarly, the above-described model can account for the ability of ligand to either promote EcR-USP, (Yao et al., 1993, supra) or destabilize VDR-RXR and T$_3$R-T$_3$R dimers (see, for example, Andersson et al., in *Nucleic Acids Res.* 20:4803–4810 (1992); Ribiero et al., in *Mol. Endocrinol.* 6:1142–1152 (1992); Ye et al., in *J. Biol. Chem.* 267:3565–3568 (1992); MacDonald et al, in *Mol. Cell Biol.* 13:5907–5917 (1993); and Cheskis and Freedman, in *Mol. Cell Biol.* 14:3329–3338 (1994)).

The restriction of RXR activity within certain heterodimers indicates that 9-cis RA responsiveness is not an obligatory consequence of heterodimerization with RXR. This allows RXR to function as both a receptor and as a heterodimerization partner, without requiring all target genes to be 9-cis RA responsive. This explains the paradox as to how RXR serves as a common subunit for receptors which display independent physiologic effects (e.g. T$_3$R, RAR, VDR).

In contrast, the ability of RXR to transduce signals when complexed with Nurr1 suggests an alternative pathway for 9-cis RA signaling. Nurr1 expression is induced by physiological stimuli (see Davis and Lau, in Mol. Cell Biol. 14:3469–3483 (1994)) including membrane depolarization and liver regeneration (Scearce et al., 1993, supra). Based on the results presented herein, it is clear that RXR contributes to the regulation of these events.

Figure 7A:
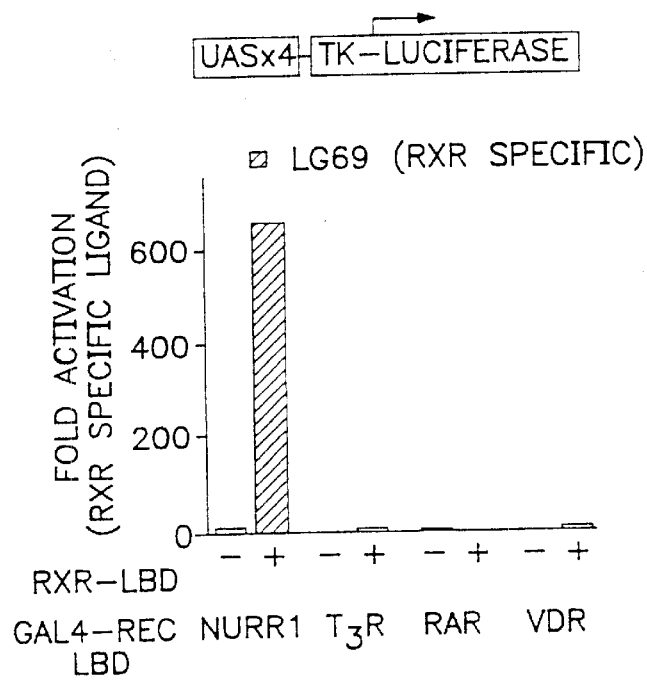
FIG. 7A presents the results of transient transfection analysis of GAL-Receptor LBD chimeras in the presence of the RXR LBD.
Figure 7B:
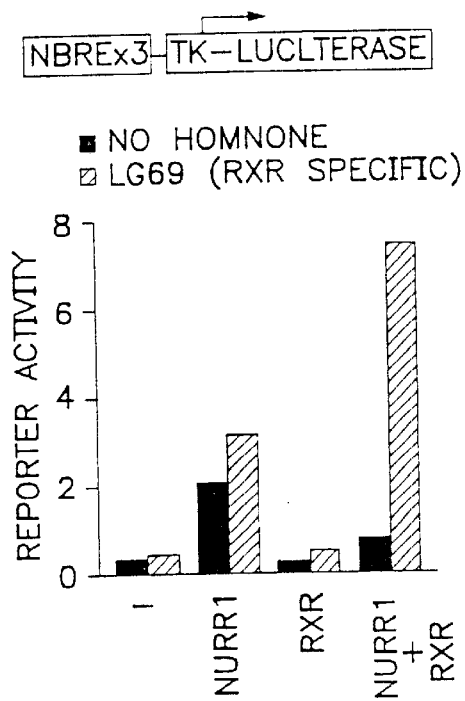
FIG. 7B presents transient transfection analysis of full-length Nurr1 and/or RXR.
Figure 7C:
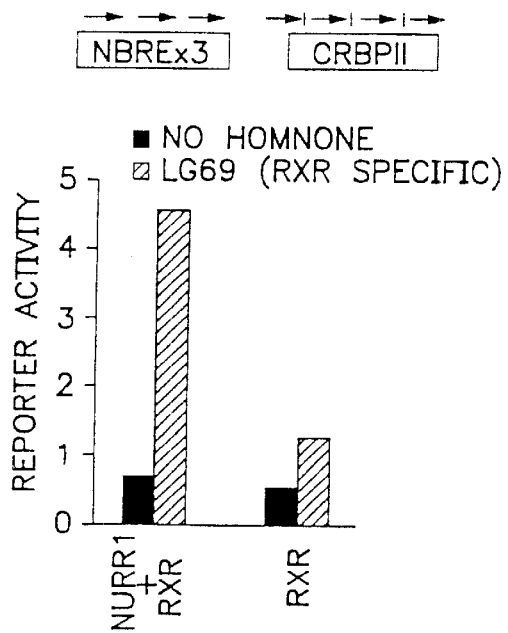
FIG. 7C presents a comparison of the responsivity of Nurr1-RXR complex, or RXR alone, in the presence and absence of RXR specific ligand in the presence of a Nurr1 specific response element (NBRE) or an RXR specific response element (CRBPII).
Figure 7D:
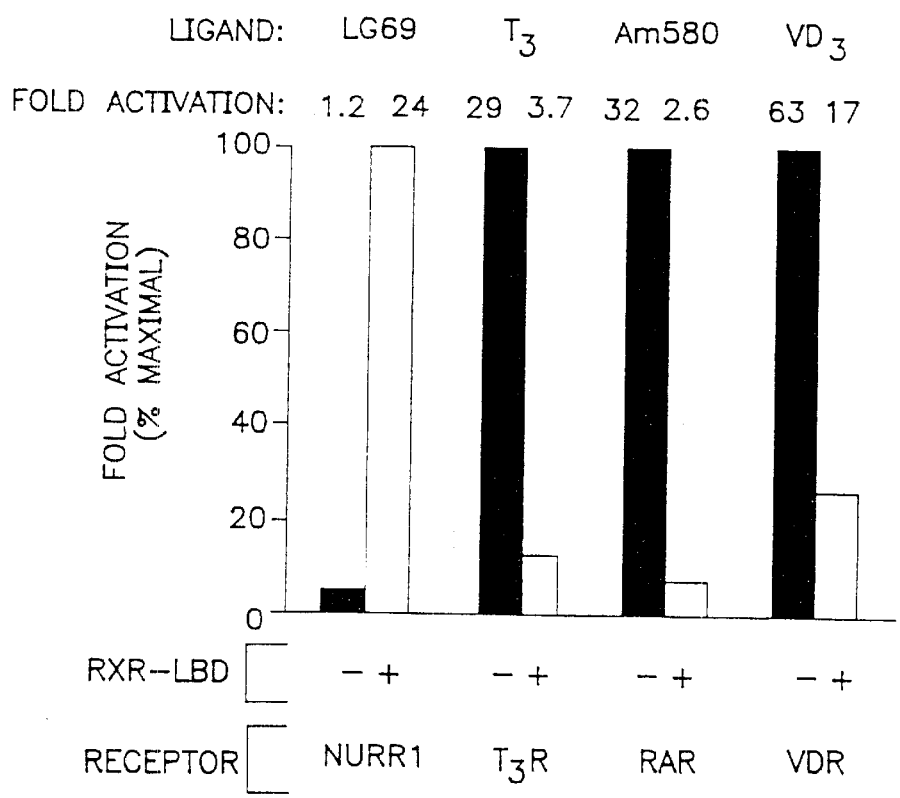
FIG. 7D demonstrates that the RXR LBD activates through Nurr1 but inhibits activation of other receptors.

Unlike previously described heterodimers, RXR functionally interact with Nurr1 in the absence of RXR- specific DNA contacts (see FIG. 7D). Indeed, the ability to tether to a DNA bound monomer is a distinguishing feature of the Nurr1-RXR heterodimer complex. As a result, an RXR mutant that is deficient in DNA binding activates through Nurr1 while it inhibits other receptor heterodimers (see FIG. 7D).

In accordance with the present invention, there are provided methods for the modulation of Nurr1 expression induced by physiological stimulus of a subject. Such method comprises administering to the subject an effective amount of a composition comprising at least the ligand binding domain of RXR. Physiological stimuli contemplated for treatment in accordance with the present invention include any event which induces production of calcium ions, cyclic AMP, ACTH, and the like.

The invention will now be described in greater detail by reference to the following non-limiting examples.

EXAMPLE 1

Cell Culture and Transfection

CV-1 cells were grown in Dulbecco's Modified Eagle's medium supplemented with 10% resin-charcoal stripped (Samuels et al., *Endocrinology* 105:80–85 (1979)) fetal bovine serum, 50 U/ml penicillin G and 50 µg/ml streptomycin sulfate (DMEM-FBS) at 37° C. in 5! $CO_2$. One day prior to transfection, cells were plated to 50–80% confluence using phenol-red free DMEM-FBS. Cells were transfected by lipofection using N-{2-(2,3)-dioleoyloxy)propyl-N,N,-trimethyl ammonium methyl sulfate} according to the manufacturer's instructions (DOTAP, Boehringer Mannheim). After 2 hours, the liposomes were removed and cells treated for 40 hours with phenol-red free DMEM-FBS alone or with the following ligands: 100–300 nM T$_3$ (L-triiodothyronine), 100 nM LG69 (4-{1-(3,5,5,8,8-pentamethyl-5,6,7,8-tetrahydro-2-napthalenyl)-1-propenyl} benzoic acid), 50–100 nM Am580 (4-(5,6,7,8-tetrahydro-5, 5,8,8-tetramethyl-2napthamido) benzoic acid) or 100 nM VD3 (1α, 25-dihydroxyvitamin D$_3$). Cells were harvested and assayed for luciferas and β-galactosidase activity. All points were performed in triplicate in each experiment and varied by less than 10%. Each experiment was repeated three or more times with similar results.

EXAMPLE 2

Expression and Reporter Constructs

For luciferase assays, response elements with HindIII overhangs were cloned into the HindIII site of the TK-LUC reporter which contains the Herpes virus thymidine kinase promoter (−105/+51). Response elements with the underlined consensus hexanucleotide sequence were as follows:
UAS$_G$×4 (i.e., 4 copies of the following sequence):
   5'-CGGAGTACTGTGTCCTCCGAGCT; SEQ ID NO:2
IRO=TREP (i.e., 1 & 2 copies of the following sequence):
   5'-TC<u>AGGTCA</u> G<u>ACCT</u>GAG; SEQ ID NO:3
DR4×2
   5'-AA<u>AGGTCA</u>CGA<u>AAGGTCA</u> CCATCCCGGGAAA <u>AGGTCA</u>CGA<u>AAGGTCA</u>CC; SEQ ID NO:4
DR5
   5'-C<u>AGGTCA</u>-CC<u>AGGAGGTCA</u>GAG; SEQ ID NO:5
DR5×2
   5'-AA<u>AGGTCA</u>CCGA<u>AAGGTCA</u> CCATCCCGG-GAAA <u>AGGTCA</u>CCGA<u>AAGGTCA</u>CC; SEQ ID NO:6
ER8
   5'-<u>TGACCT</u>TTCTCTCC <u>AGGTCA</u>; SEQ ID NO:7
BRE×3 (i.e., 3 copies of the following sequence):
   5'-GAGTTTAA<u>AAGGTCA</u> TGCTCAATTTTC; SEQ ID NO:8
CRBPII
   5'-GTCAC<u>AGGTCACAGGTCACAGGTCAC</u> AGTTCA; SEQ ID NO:9
MLV-DR4×2 (i.e., 2 copies of the following sequence):
   5'-AA<u>GGTTCA</u>CGA<u>GGTTCA</u>CGT; SEQ ID NO:10.
All mammalian expression vectors were derived from pCMX (Umesono et al., 1991, supra) which contains the CMV promoter/enhancer followed by a bacteriophage T7 promoter for transcription in vitro. pCMX expression vectors for T3R$_β$, hRARα (Umesono et al., 1991, supra) and hRXRα (Yao et al., 1993, supra) were used as previously described. CMX-Nurr1 (provided by Thomas Perlmann), an expression vector for full-length mouse Nurr1, was cloned by inserting the BglII-XhoI fragment from pBS34-1 (excised from λZAP34) (see Law et al., 1992, suora) into pCMX. The VP16-RXR fusion contains the 78 amino acid transactivation domain of Herpes VP16 from pVP16C1 (Novagen) fused N-terminal to the full-length hRXRα.

GAL4 fusions were made by fusing the following receptor ligand binding domains to the C-terminal end of the yeast GAL4 DNA binding domain (amino acids 1–147) from pSG424 (see Sadowski and Ptashne, in *Nucleic Acids Res.* 17:7539 (1989)): human RXRα LBD (Glu 203–Thr 462); mouse Nurr1 (Cys 318–Phe 598); human $T_3R\beta$ (Leu 173–Asp 456); human RARα (Glu 156–Pro 462); and human VDR (Glu 92–Ser 427). The LBD expression constructs contain the SV40 TAg nuclear localization signal (APKKKRKVG; SEQ ID NO:11) fused upstream of the human $T_3R\beta$ LBD (Leu 173–Asp 456), HRARα LBD (Glu 156–PRO 46 ) or the human RXRα LBD (Glu 203–Thr 462). CMx-βgal contains the *E. coli* β-galactosidase coding sequences derived from pCH110 (Pharmacia) cloned into pCMX.

Figure 5A:
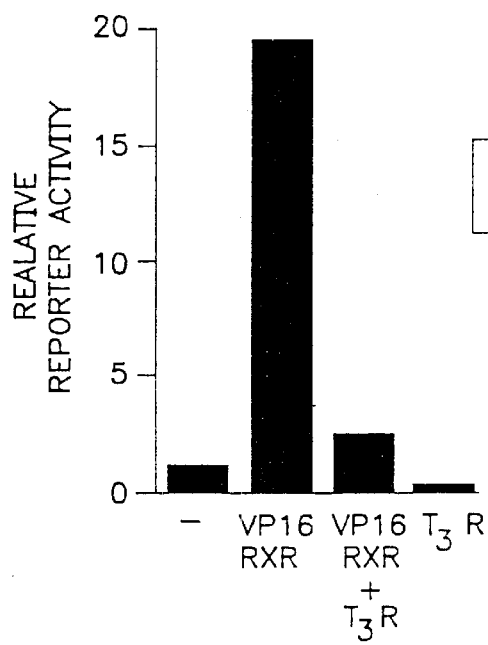
FIG. 5 illustrates the ability of $T_3R$ and RAR to suppress transcription of a constitutively active RXR derivative (i.e., VP16-RXR).
Figure 5B:
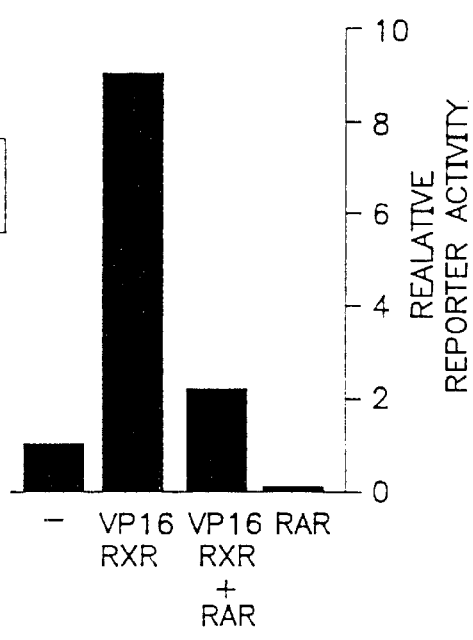

In the left panel of FIG. 5, CV-1 cells were transfected with the following plasmids: IRO TK-LUC (SEQ ID NO:3; 300 ng/$10^5$ cells), CMX-βgal (500 ng/$10^5$ cells) alone (–) or with CMX-VP16-RXRα (100 ng/$10^5$ cells) and/or CMX-hRARα (50 ng/$10^5$ cells) as indicated. No ligand treatment was employed. Luciferase activity was normalized to the β-galactosidase internal control. In each experiment, the normalized activity obtained in the presence of VP-RXR, $T_3R$ or RAR is plotted as activity relative to the reporter alone, which was defined to have a relative activity of 1.

EXAMPLE 3

Ligand Binding Assays

Bacterially expressed proteins were used for ligand binding assays. GST-hRXRα (see Mangelsdorf et al., in *Cell* 66:555–561 (1991)), chicken $T_3R\alpha 1$ (see Forman et al., in *Mol. Endocrinol.* 6:429–442 (1992)) and human RARα (Forman et al., 1992, supra) were expressed and purified to near homogeneity as previously described. GST-RXR (150 ng) or a GST control (150 ng) were incubated with or without approximately 500 ng of $T_3R$ or RAR in the presence of 50 nM [$^3$H]-ligands (LG69, 56 Ci/mmol; at-RA, 49 Ci/mmol; 9-cis RA, 29 Ci/mmol), 3 ng/μl poly dI-dC, 50 fmol/μl of the indicated oligonucleotide, 10 μl of 50% (v/v) epoxy-linked glutathione-sepharose Sigma) in ligand binding buffer (25 mM Tris, pH 7.8, 0.5% C PS, 100 mM KCl, 8% Glycerol, 1 mM DTT).

Where indica ed (see, for example, FIG. 6), unlabeled ligands were added as follows: LG69, 2 μM; Am580, 2 μM; $T_3$, 1 μM. The reaction was mixed for 30 minutes at 25° C. and then chilled to 4° C. for 10 minutes. The glutathione-sepharose beads were washed three times in ligand binding buffer and the amount of [$^3$H]bound was determined in a liquid scintillation counter. Background binding was determined with the GST control and represented 3–5% of the total binding seen with GST-RXR.

EXAMPLE 4

RXR Responsiveness is Diminished in $T_3$R-RXR and RAR-RXR heterodimers

Figure 2A:
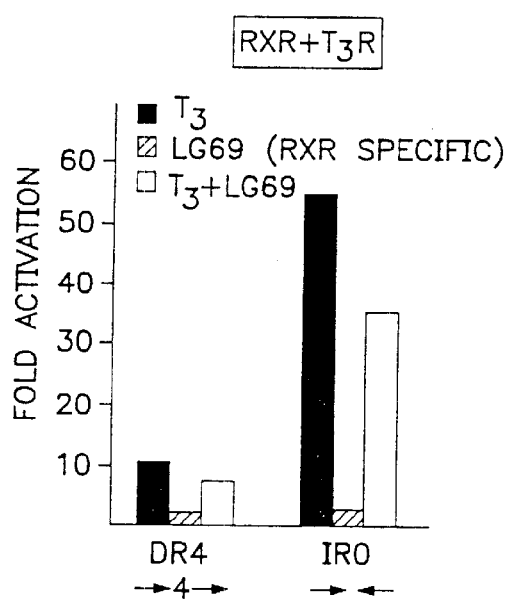
FIG. 2 illustrates the differential modulation of RXR response by $T_3R$ (shown in FIG. 2A) and RAR (shown in FIG. 2B).
Figure 2B:
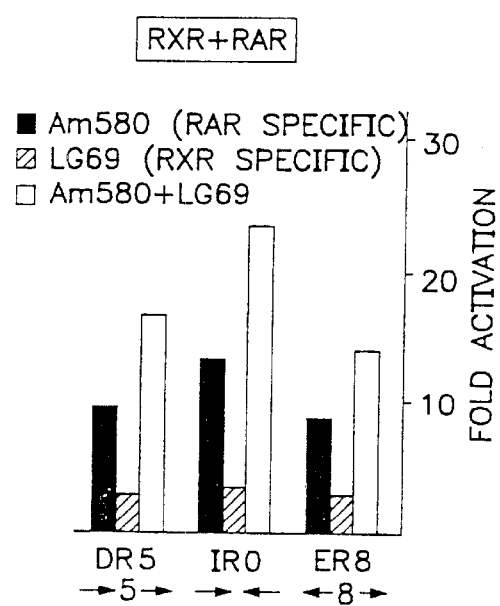

Since $T_3R$ an RAR function as heterodimers with RXR, RXR responsiveness was examined in the context of RXR-$T_3R$ and RXR-RAR heterodimers. Attention is directed to FIG. 2, wherein transient transfection analysis of $T^3$R-RXR and RAR-RXR heterodime is described. Reporter constructs employed contain the HRE indicated in the figure, cloned upstream of the TK-LUC reporter. In the left panel of the figure, CV-1 cells were transfected with the following plasmids: HREx2—K-LUC (300 ng/$10^5$ cells), CMX-h$T_3R\beta$ (20 ng/$10^5$ cells), CMX-hRXRα (20 ng/$10^5$ cells) and the internal control CMX-βgal (500 ng/$10^5$ cells). Cells were treated without ligand or with 100 nM $T_3$, 100 nM LG69 or 100 nM $T_3$+100 nM LG69.

In the right panel of FIG. 2, cells were transfected with HREx1 TK-LUC (300 ng/$10^5$ cells), CMX-hRARα (50 ng/$10^5$ cells) CMX-hRXRα (50 ng/$10^5$ cells) and CMX-βgal (500 ng/$10^5$ cells). Cells were treated without ligand or with 50 nM A580, 100 nM LG69 or 50 nM Am580+100 nM LG69. Normalize luciferase activity was determined and plotted as fold-activation relative to untreated cells.

Although cells transfected with both $T_3R\beta$ and RXRα expression vectors were responsive to $T_3$, they were surprisingly not responsive to the RXR specific ligand LG69 (see FIG. 2; Boehm et al., in *J. Med. Chem.* 37:408–414 (1994)). Treatment of these cells with both $T_3$ and LG69 did not result in further stimulation of the $T_3$ response, rather the response to $T_3$ was somewhat reduced. Similarly, cells simultaneously transfected with RAXα and RXRα expression vectors responded to the RAR-specific ligand Am580, but remained unresponsive to LG69. In contrast, treatment with Am580+LG69 resulted n increased transcriptional activity over that seen with 580 alone.

EXAMPLE 5

Suppression of RXR Activity is Mediated by the LBD

Since RXR homodimers are activated RXR agonists, the results presented above suggest that RXR activity is suppressed in unliganded RXR-$T_3R$ and RXR-RAR heterodimers. It is suspected that heterodimerization within the LBD (see FIG. 1) could induce an allosteric change in the RXR LBD that blocks its ability to bind ligand and/or transactivate. To test this hypothesis, a system was developed to examine the responsiveness of RXR-containing heterodimers in a manner that relies solely on interactions between the LBDs.

Thus, a chimeric protein was constructed containing the yeast GAL4 DBD linked to the RXR LBD (GAL-RXR). The ability of this RXR-chimera to respond to LG69 was initially examined in the presence of truncated receptors containing the LBDs of $T_3R$ or RAR. Thus, transient transfection analysis of GAL-RXR LBD was carried out in the presence of $T_3R$, RAR or VDR LBDs. Reporter constructs contained 4 copies of the $UAS_G$ cloned upstream of the TK-LUC reporter. V-l cells were tranfected with $UAS_G$×4 TK-LUC (SEQ ID NO:2; 300 ng/$10^5$ cells), CMX-GAL-RXR (100 ng/$10^5$ cells), CMX-βgal (500 ng/$10^5$ cells) alone or with either CMX-$T_3R$ LBD, CMX-RAR LB or CMX-VDR LBD (100 ng/$10^5$ cells). Following transfection, cells were treated without ligand or with 100 nM LG69, 100 nM $T_3$, 50 nM Am580 or 100 nM VD3. Normalized luciferase activity was determined and plotted as reporter activity (see FIG. 3).

Figure 3:
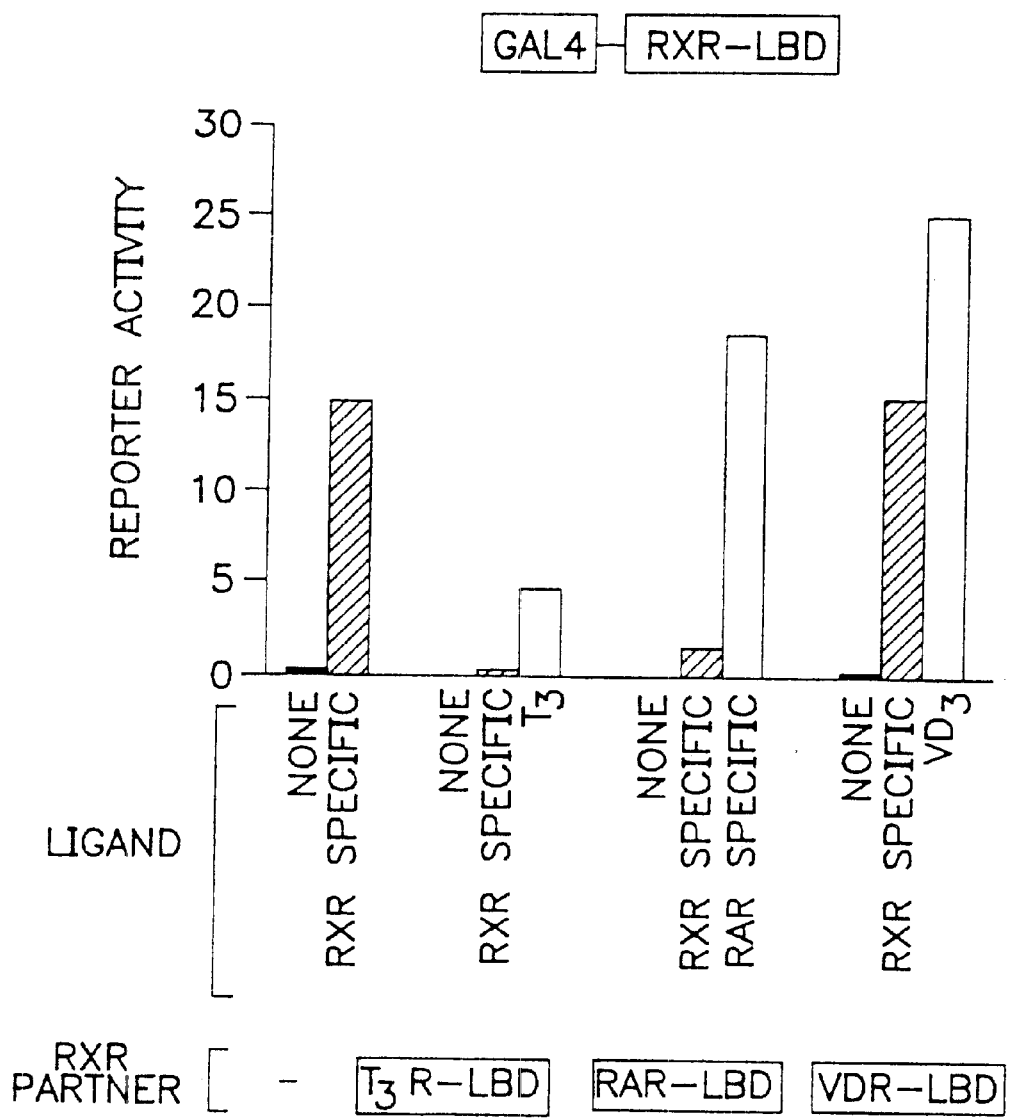
FIG. 3 illustrates the differential modulation of RXR transcriptional activity by the LBDs of $T_3R$, RAR and VDR.

Although GAL-RXR activated the $UAS_G$ reporter in response to LG69, the absolute levels of induced and uninduced activity were dramatically suppressed by both $T_3R$ and RAR LBDs (see FIG. 3). In contrast, the VDR LBD failed to suppress RXR responsiveness. These results indicate that suppression of RXR by unliganded T$_3$R and RAR is mediated solely by interactions between the LBDs of these receptors.

These results are consistent with previous experiments which have shown that receptor LBDs remain tethered to the GAL-RXR LBD in cells (see, for example, Nagpal et al., 1993, supra). Thus, it was next sought to determine whether the tethered LBDs can activate transcription in response to their specific ligands. As seen in FIG. 3, the T$_3$R, RAR and VDR LBDs conferred ligand-dependent activation upon GAL-RXR, but not GAL4 alone. Thus, receptor LBDs tethered to RXR provide all the functions required for ligand-dependent transcriptional activation in the absence of direct DNA contact.

Figure 4A:
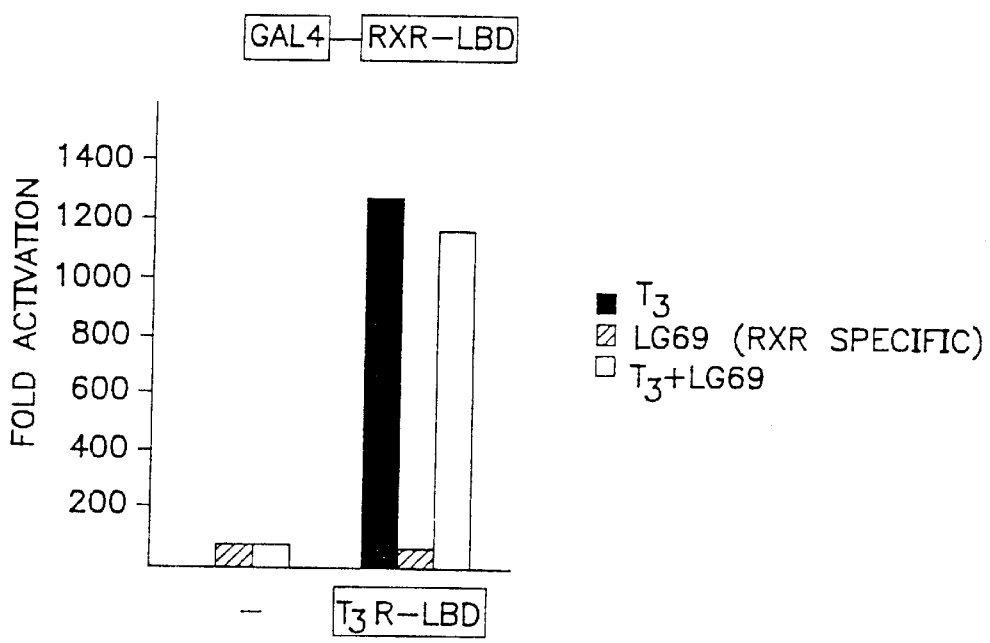
FIG. 4A illustrates the differential modulation of RXR transcriptional activity by the LBD of $T_3R$, wherein cells treated according to FIG. 3 were additionally treated with $T_3$ (i.e., $T_3R$ ligand) and LG69 (i.e., an RXR specific ligand). Normalized reporter activity was determined and plotted as fold-activation relative to untreated cells.
Figure 4B:
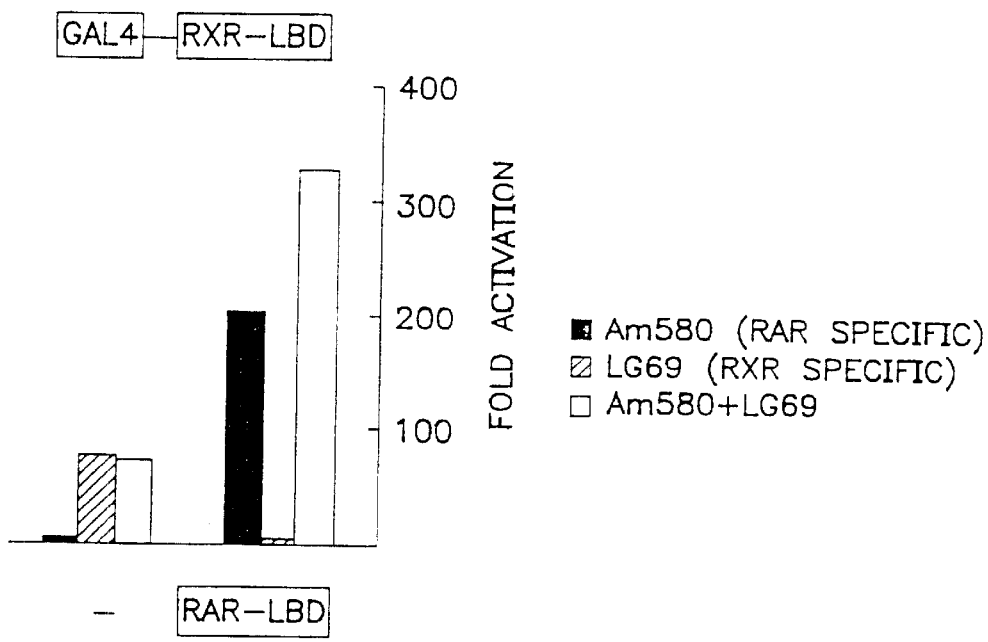
FIG. 4B illustrates the differential modulation of RXR transcriptional activity by the LBD of RAR, wherein cells treated according to FIG. 3 were additionally treated with AM580 (i.e., an RAR specific ligand) and LG69. Normalized reporter activity was determined and plotted as fold-activation relative to untreated cells.

The experiment described with respect to FIG. 3 was also performed with the combination of RXR-specific ligand (e.g., LG69) and T$_3$R or RAR specific ligand (see FIG. 4, which illustrates the differential modulation of RXR transcriptional activity by the LBD of T$_3$R. Thus, cells treated according to the procedure described above with respect to FIG. 3 were additionally treated with 100 nM T$_3$+100 nM LG69 (see FIG. 4A) or 50 nM AM580+100 nM LG69 (see FIG. 4B). Normalized luciferase activity was determined and plotted as fold-activation relative to untreated cells.

In order to compare the effects of T$_3$R and RAR LBDs on LG69 inducibility of GAL-RXR, these data were replotted as fold-induction. Comparison of FIGS. 2 and 4 indicate that the effects ligand-occupied T$_3$R and RAR are qualitatively similar, regardless of whether the full-length receptors or their LBDs are used. Note that the T$_3$R LBD led to a coordinate reduction in both basal and LG69-induced activities of GAL-RXR, hence the fold response to LG69 was only modestly inhibited from 69-fold (see FIG. 4A, GAL-RXR alone) to 57-fold by the T$_3$R LBD (FIG. 4B, GAL-RXR +T$_3$R LBD). Addition of T$_3$ resulted in strong 5 activation of T$_3$R and the combination of T$_3$+LG69 resulted in slightly less activity than with T$_3$ alone. In contrast to T$_3$R, unliganded LBD strongly suppressed the fold-responsiveness of GAL-RXR to LG69. Treatment with Am580+LG69 resulted in increased transcriptional activity over that seen with AM 80 alone suggesting that RXR responsiveness to LG69 may be restored by addition of the RAR agonist Am580 (FIG. 4B).

EXAMPLE 6

RAR and T$_3$R Differentially Suppress the Ligand Binding Activity of RXR

In addition to decreasing basal and activated transcription, RAR also blocks the ability of RXR to respond to its ligand. Thus, the possibility that RXR is incapable of binding ligand when tethered to RAR was examined. A bacterially expressed glutathione-S-transferase-RXRa fusion protein (GST-RXR) was incubated with recombinant T$_3$R or RAR in the presence of radiolabeled RXR ligands. The amount of ligand bound to RXR or RXR-containing heterodimers was quantitated using glutathionesepharose as an affinity probe. In the left panel of FIG. 6A, purified GST-hRXRα was incubated with 50 nM [$^3$H]LG69 (56 Ci/mmol) ad the optimized RAR response element 5'-GCAAA AGGTCA AAAAG AGGTCA TGC-3'; SEQ ID NO:12; Kurokawa et al., Genes Dev. 7:1423–1435 (1993)) alone or with 2 pM LG69, 2 µM Am580. In th right panel of FIG. 6A, purified GST-hRXRα and the RAR response element (SEQ ID NO:12) were incubated with 25 nM [$^3$H]at-RA (49 Ci mmol) without or with 500 ng of hRARα. The amount of specifi-cally bound [$^3$H]label was then determined employing standard techniques as previously described.

Figure 6A:
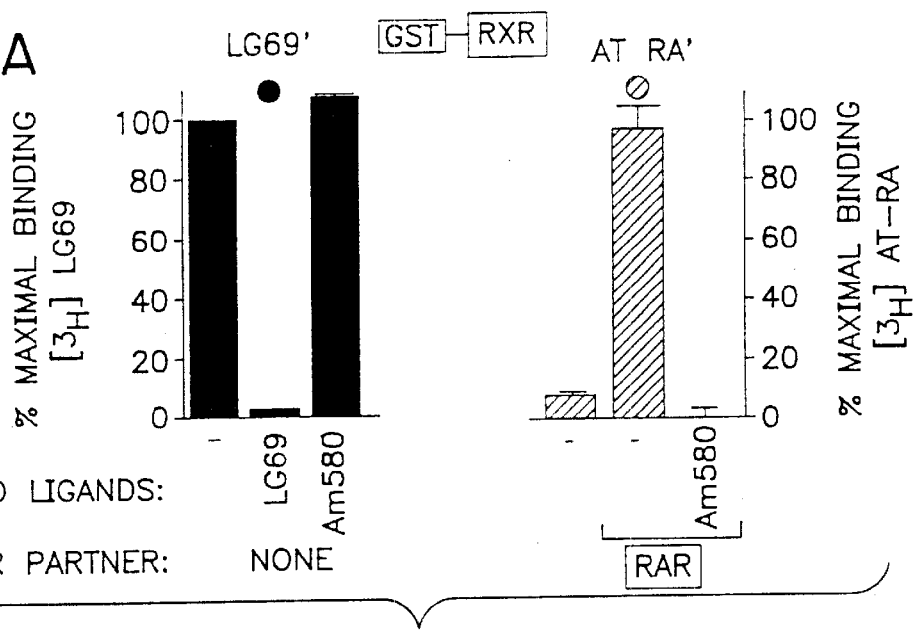
FIG. 6A illustrates the binding of LG69 (an RXR specific ligand), at -RA (all-trans retinoic acid, an RAR specific ligand) and Am580 (an RAR specific ligand) to RXR and/or RAR.

As expected binding of [$^3$H]LG69 to GST-RXR was specifically completed by unlabeled LG69, but not by the RAR-specific ligand A 580 (see FIG. 6A, right panel); specific binding of [3H]all-trans RA (at-RA) was observed when GST-RXR was mixed with excess RAR (see FIG. 6A, right panel). A quantitation of the amount of specifically bound [$^3$H]LG69, [$^3$H]at RA or [$^{125}$I]T$_3$ indicates that GST-RXR could be saturated with approximately equimolar amounts of RAR or T$_3$R, respectively. Electrophoretic mobility shift experiments indicate that ligands do not alter the binding activity of T$_3$R-RXR or RAR-RXR heterodimers.

Next, the ligand binding activity of RXR was examined in the presence of RAR-T$_3$R. Thus, purified GST-hRXRα and 50 nM [$^3$H]LG69 (56 Ci/mmol) were incubated alone or with 500 ng of hRARα or chicken T$_3$Rα1 and the optimized RAR response element (SEQ ID NO:12) or the optimized T$_3$R response element 5'-GCAAA AGGTCA AATA AGGTCA CGT-3'; SEQ ID NO:13; Kurokawa et al., supra), respectively. Where indicated, unlabeled T$_3$ was added to a concentration of 1 µM. Specifically bound [$^3$H]LG69 was determined.

Surprisingly, addition of RAR resulted in a dramatic (<85%) decrease in the amount of [$^3$H]LG69 bound to GST-RXR (see FIG. 6B) indicating that the ligand binding potential of RXR is reduced in the RXR-RAR heterodimer. These findings account for the ability of unoccupied RAR to suppress the ligand inducibility of RXR (see FIG. 4B).

Figure 6B:
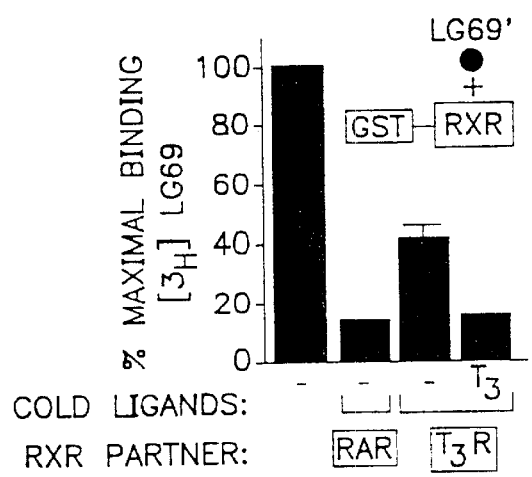
FIG. 6B illustrates that the binding of LG69 to RXR is reduced in RAR-RXR and $T_3R$-RXR heterodimers.

Similar experiments were performed on the RXR-T$_3$R heterodimer. In contrast to RAR, unliganded T$_3$R led to a modest reduction in [$^3$]LG69 binding. However, ligand binding was strongly diminished upon addition of T$_3$ (FIG. 6B). These findings are consistent with the observation that unoccupied T$_3$R results in a modest suppression of RXR inducibility, whereas no induction is elicited when T$_3$R is occupied by T$_3$ (FIG. 4 ).

The transfection experiments summarized in FIGS. 2 and 4B indicate that RAR-RXR heterodimers exhibit RXR responsiveness only in the presence of an RAR ligand, suggesting that RXR binding activity may be restored by RAR ligands. To test this hypothesis, the observation that 9-cis RA binds with high affinity to both RAR and RXR (Allegretto et al., 1993; Allenby et al., 1993) was applied as follows. Thus, GST-RXR/RAR heterodimers were allowed to form in the presence of [$^3$H]9-cis RA. Reactions were performed as described above with reference to FIG. 6A, using both GST-hRXRα and hRARα with 50 nM [$^3$H]9-cis RA (29 Ci/mmol). Specifically bound [$^3$H]9-cis RA was determined in the absence or presence of 2 µM LG69 and/or 2 µM Am580. In all experiments, maximal binding was in the range of 200–300 fmol of [$^3$H]ligand.

Figure 6C:
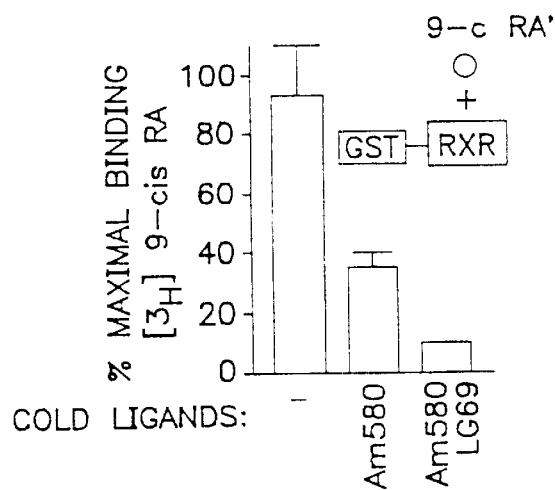
FIG. 6C illustrates that competition of [$^3$H]9-cis RA bound to RXR-RAR heterodimers requires RAR and RXR ligands.

Although Am580 fully competed with [$^3$H]at-RA for binding to GST-RXR/RAR heterodimers (FIG. 6A, right panel), Am580 resulted in only a partial decrease in [$^3$H]9-cis RA binding (see FIG. 6C). Nearly complete competition was observed by addition of both Am580 and the RXR-specific ligand LG6 (see FIG. 6C), suggesting that RXR can bind ligand, provided the RAR LBD is occupied. These findings are consistent with the restoration of RXR responsiveness in RAR-occupied heterodimers (FIG. 4B).

EXAMPLE 7

Identification of a Novel RXR-permissive Heterodimer

Since RXR serves as a silent partner in the $T_3R$ and RAR pathways, it was next investigated whether RXR could serve as an active component in other complexes. To search for such complexes, the LBD of a number of nuclear receptors were fused to the GAL4 DBD, and tested to determine whether the RXR LBD could confer LG69 responsiveness upon these GAL-LBD chimeras. Thus, CV-1 cells were transfected with $UAS_g \times 4$ TK-LUC (SEQ ID NO:2; 300 ng/$10^5$ cells), CMX-βgal (500 ng/$10^5$ cells) and the indicated CMX-GAL-receptor LBD construct (100 ng/$10^5$ cells) with or without CMX-RXR LBD (100 ng/$10^5$ cells). Following transfection, cells were treated without ligand or with 100 nM LG69. Normalized luciferase activity was determined and plotted as fold-activation relative to untreated cells.

As expected LG69 responsiveness was not seen when the RXR LBD was expressed alone, or with GAL-$T_3R$ and GAL-RAR (see FIG. 7A). Similarly, LG69 inducibility was not observed with chimras containing the LBDs of VDR (see FIG. 7A) or several ther members of the nuclear receptor superfamily. Unexpectedly, strong responsiveness to LB69 was observed when the RXR-LBD was co-expressed with a GAL-Nurr1 chimera (see FIG. 7A). These results suggest that the LBDs of Nurr1 and RXR form a novel heterodimer complex which promotes potent RXR responsiveness.

Nurr1 (also known as RNR-1, NOT, HZF-3), the β isoform of NGFI-b (also known as nur77, N10, NAK-1, TR3), is reported to be a constitutively active orphan receptor that binds as a high-affinity monomer to an AAAGGTCA (SEQ. ID. No.:14) core-site (NBRE) (see, for example, Law et al., 1992, supra; Wilson et al., 1992, supra Scearce et al., 1993, supra; and Wilson et al., 1993, supra). This prompted further investigation as to when full-length Nurr1 and RXR could interact productively on the NBRE.

Thus, CV-1 cells were tranfected with NBREx3 TK-LUC (SEQ ID NO:8; 300 ng/$10^5$ cells), CMX-βgal (500 ng/$10^5$ cells), alone or with CMX-Nurr (100 ng/$10^5$ cells) and CMX-hRXRu (100 ng/$10^5$ cells) as indicated in FIG. 7B. Following transfection, cells were treated with or without 100 nM LG69. Normalized luciferase activity was determined and plotted as reporter activity.

Consistent with published results (see, for example, Scearce et al., 1993, supra), Nurr1 constitutively activates the NBRE reporter (see FIG. 7B), but was not responsive to LG69 (FIG. 7B). RXR, which does not bind to the NBRE, did not activate this reporter. However, when Nurr1 and RXR are co-expressed, the constitutive activity of Nurr1 is suppressed, and the complex becomes strongly responsive to LG69 (FIG. 7B). Similar results were obtained with RXRα, RXRβ and RXRγ.

The ability of the Nurr1-RXR heterodimer complex to transduce RXR Signals suggested the desirability of comparing the activity of this complex with that of RXR on an established RXR response element (CRBPII, cellular retinol binding protein II; see Mangelsdorf et al., 1991, supra). Using sub-optimal amounts of RXR-expression vector, the CRBPII reporter was compared with a 3-copy NBRE reporter as follows. Cells were transfected as described with respect to FIG. 7B, but with a 5-fold lower amount of CMX-hRXRα (20 ng/$10^5$cells). CRBPII TK-LUC (SEQ ID NO:9; 300 ng/$10^5$ cells) was used where indicated.

Since RXR was limiting in this assay, only minimal activation of the CRBPII reporter was observed (see FIG. 7C). In contrast, Nurr1-RXR displayed a potent response to LG69, despite the fact that the NBRE reporter contains 1 less core-binding site than CRBPII (see FIG. 7C). Thus, Nurr1-RXR can efficiently transduce RXR signals. However, unlike other heterodimers, the Nurr1-RXR complex is strongly responsive to LG69 and 9-cis RA, suggesting that this complex establishes a novel signaling pathway for 9-cis RA.

EXAMPLE 8

Nurr1 Does not Require the RXR DBD for Coupling

The Nurr1-RXR complex is unique in several ways. First, the Nurr1 DBD recognizes its response element in the absence of RXR (see, for example, Wilson et al., 1992, supra; Scearce et al., 1993, supra; and Wilson et al ., 1993, supra). Second, the monovalent NBRE serves as a response element for a multimeric Nurr1-RXR complex (see FIG. 7B). These observations raise the possibility that RXR associates with BRE-bound Nurr1 in the absence of RXR-specific DNA contacts. Such behavior would be in sharp contrast with $T_3R$, RAR and VDR, which rely on RXR-specific contacts to recognize hormone response elements. Indeed, RXR mutants lacking the DBD associate with wild-type RAR; however, these complexes do not bind DNA or activate transcription (see Minucci et al., in *Mol. Cell Biol.* 14:360–372 (1994)).

This prompted an investigation of the question of whether the RXR DBD is required for activation through the Nurr1 pathway. Thus, CV-1 cells were transfected with TK-LUC reporters (300 ng/$10^5$ cells), CMX-βgal (500 ng/$10^5$ cells) and the indicated CMX-receptor construct (20 ng/$10^5$ cells; see FIG. 7D)with or without CMX-RXR-LBD (100 ng/$10^5$ cells). The following receptor, reporter, ligand combinations were used: Nurr1, NBREx3 (SEQ ID NO:8), 100 nM LG69; $hT_3R\beta$, MLVx2 (SEQ ID NO:10), 100 nM $T_3$; hRARα, DR5x2 (SEQ ID NO:6), 100 nM Am580; hVDR, SPP1x3, 100 nM $VD_3$. Normalized luciferase activity was determined and plotted as percent of maximal fold-activation where 100% is defined as the fold activation by $T_3R$, RAR, VDR, the RXR LBD, or Nurr1+RXR LBD. The actual fold-activation values are shown above each bar in the figure.

As shown in FIG. 7D, the RXR LBD is sufficient to confer strong LG69 responsiveness upon Nurr1. In contrast, the RXR LBD acts as a dominant-negative inhibitor of wild-type VDR, $T_3R$ and RAR (FIG. 7D). These findings indicate that the RXR DBD is not required for ligand-dependent activation of Nurr1-RXR, a property that further distinguishes this novel complex from previously described RXR-containing complexes.

While the invention has been described in detail with reference to certain preferred embodiments thereof, it will be understood that modifications and variations are within the spirit and scope of that which is described and claimed.

That which is claimed is:

1. An isolated heterodimer complex comprising RXR and a silent partner which dimerizes with RXR, wherein said silent partner is a member of the steroid/thyroid hormone receptor superfamily of receptors which, in the absence of RXR, binds to DNA as a monomer and there by constitutively activates transcription of a target gene operatively associated with said DNA.

2. A heterodimer complex according to claim 1 wherein said silent partner is Nurr1.

3. A heterodimer complex according to claim 1 wherein RXR is selected from the group consisting of RXRα, RXRβ and RXRγ.

4. A heterodimer complex according to claim 3 wherein RXR is RXRα.

5. A heterodimer complex according to claim 3 wherein RXR is RXRβ.

6. A heterodimer complex according to claim 3 wherein RXR is RXRγ.

7. A heterodimer complex according to claim 1 wherein said silent partner comprises a DNA binding domain that preferentially binds to a nucleotide sequence comprising SEQ ID NO:14.

8. A heterodimer complex according to claim 1 wherein said silent partner is NGFI-B.

9. An isolated heterodimer complex comprising the ligand binding domain of RXR and Nurr1.

10. An isolated heterodimer complex comprising the ligand binding domain of RXR and NGFI-B.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 71 amino acids
       (B) TYPE: amino acid
       (C) STRANDEDNESS: single
       (D) TOPOLOGY: linear (xi) SEQUENCE DESCRIPTION: SEQ ID NO:1:

Cys Xaa Xaa Cys Xaa Xaa Asp Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Xaa Cys Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
65                  70

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:2:

CGACGGAGTA CTGTCCTCCG AGCT                                          24

(2) INFORMATION FOR SEQ ID NO:3:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:3:

TCAGGTCATG ACCTGAG                                                  17

(2) INFORMATION FOR SEQ ID NO:4:

(i) SEQUENCE CHARACTERISTICS:
       (A) LENGTH: 48 base pairs
       (B) TYPE: nucleic acid
       (C) STRANDEDNESS: single
       (D) TOPOLOGY: linear (xi) SEQUENCE DESCRIPTION: SEQ ID NO:4:

AAAGTCACGA AAGGTCACCA TCCCGGGAAA AGGTCACGAA AGGTCACC                48

(2) INFORMATION FOR SEQ ID NO:5:

(i) SEQUENCE CHARACTERISTICS:
       (A) LENGTH: 21 base pairs
       (B) TYPE: nucleic acid
       (C) STRANDEDNESS: single (D) TOPOLOGY: linear (xi) SEQUENCE DESCRIPTION: SEQ ID NO:5:

CAGGTCACCA GGAGGTCAGA G                                              21

(2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:6:

AAAGGTCACC GAAAGGTCAC CATCCCGGGA AAAGGTCACC GAAAGGTCAC C              51

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

TGACCTTTCT CTCCAGGTCA                                                20

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:8:

GAGTTTAAAA GGTCATGCCT CAATTTTC                                       28

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:9:

GTCACAGGTC ACAGGTCACA GGTCACAGTT CA                                  32

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

AAGGTTCACG AGGTTCACGT                                                20

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:11:

Ala Pro Lys Lys Lys Arg Lys Val Gly
 1               5

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:12:

GCAAAAGGTC AAAAAGAGGT CATGC                                              25

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:13:

GCAAAAGGTC AAATAAGGTC ACGT                                               24

(2) INFORMATION FOR SEQ ID NO:14:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (xi) SEQUENCE DESCRIPTION: SEQ ID NO:14:

AAAGGTCA                                                                  8